(12) United States Patent
Westlund et al.

(10) Patent No.: US 12,179,014 B2
(45) Date of Patent: Dec. 31, 2024

(54) TRANSVENOUS PHRENIC NERVE STIMULATION SYSTEM

(71) Applicant: ZOLL RESPICARDIA, INC., Minnetonka, MN (US)

(72) Inventors: Randy W. Westlund, River Falls, WI (US); Mark Gelfand, New York, NY (US)

(73) Assignee: ZOLL RESPICARDIA, INC., Minnetonka, MN (US)

( * ) Notice: Subject to any disclaimer, the term of this patent is extended or adjusted under 35 U.S.C. 154(b) by 558 days.

(21) Appl. No.: 16/525,060

(22) Filed: Jul. 29, 2019

(65) Prior Publication Data

US 2019/0351229 A1   Nov. 21, 2019
US 2022/0212005 A9   Jul. 7, 2022

Related U.S. Application Data

(63) Continuation of application No. 12/150,654, filed on Apr. 30, 2008, now Pat. No. 10,406,366, which is a continuation-in-part of application No. 11/601,150, filed on Nov. 17, 2006, now Pat. No. 8,244,359.

(60) Provisional application No. 60/926,910, filed on Apr. 30, 2007, provisional application No. 60/743,326, filed on Feb. 21, 2006, provisional application No. 60/743,062, filed on Dec. 21, 2005, provisional application No. 60/737,808, filed on Nov. 18, 2005.

(51) Int. Cl.
*A61N 1/05* (2006.01)
*A61N 1/36* (2006.01)
*A61N 1/368* (2006.01)

(52) U.S. Cl.
CPC ............ *A61N 1/0558* (2013.01); *A61N 1/05* (2013.01); *A61N 1/0551* (2013.01); *A61N 1/3605* (2013.01); *A61N 1/3611* (2013.01); *A61N 1/3601* (2013.01); *A61N 1/3684* (2013.01)

(58) Field of Classification Search
CPC .. A61N 1/0551; A61N 1/0558; A61N 1/3605; A61N 1/3601; A61N 1/3684; A61N 1/3611; A61N 1/05
See application file for complete search history.

(56) References Cited

U.S. PATENT DOCUMENTS

| | | | |
|---|---|---|---|
| 4,129,125 A | 12/1978 | Lester et al. |
| 4,169,479 A | 10/1979 | Muto |
| 4,827,935 A | 5/1989 | Geddes et al. |
| 4,830,008 A | 5/1989 | Meer |
| 5,056,519 A | 10/1991 | Vince |
| 5,146,918 A | 9/1992 | Kallok et al. |

(Continued)

FOREIGN PATENT DOCUMENTS

| | | |
|---|---|---|
| EP | 1588735 A1 | 10/2005 |
| EP | 2371416 A1 | 10/2011 |
| WO | 2008092246 A1 | 8/2008 |

OTHER PUBLICATIONS

Javaheri, Shahrokh, MD, CPAP Should Not be Used for Central Sleep Apnea in Congestive Heart Failure Patients, Journal of Clinical Sleep Medicine, vol. 2. No. 4, 2006.

(Continued)

*Primary Examiner* — Pamela M. Bays
(74) *Attorney, Agent, or Firm* — Lando & Anastasi, LLP

(57) ABSTRACT

A lead system and method of use for treating breathing disorders by the transvenous stimulation of the phrenic nerve.

13 Claims, 4 Drawing Sheets

(56) References Cited

U.S. PATENT DOCUMENTS

| | | | |
|---|---|---|---|
| 5,170,802 A | 12/1992 | Mehra | |
| 5,174,287 A | 12/1992 | Kallok et al. | |
| 5,184,621 A | 2/1993 | Vogel et al. | |
| 5,211,173 A | 5/1993 | Kallok et al. | |
| 5,265,604 A | 11/1993 | Vince | |
| 5,483,969 A | 1/1996 | Testerman et al. | |
| 5,485,851 A | 1/1996 | Erickson | |
| 5,531,781 A | 7/1996 | Alferness et al. | |
| 6,006,134 A | 12/1999 | Hill et al. | |
| 6,132,384 A | 10/2000 | Christopherson et al. | |
| 6,212,435 B1 | 4/2001 | Lattner et al. | |
| 6,266,564 B1 | 7/2001 | Hill et al. | |
| 6,301,507 B1 * | 10/2001 | Bakels | A61N 1/056 607/122 |
| 6,360,740 B1 | 3/2002 | Ward et al. | |
| 6,415,183 B1 | 7/2002 | Scheiner et al. | |
| 6,449,507 B1 | 9/2002 | Hill et al. | |
| 6,456,863 B1 | 9/2002 | Levin et al. | |
| 6,463,327 B1 | 10/2002 | Lurie et al. | |
| 6,532,388 B1 | 3/2003 | Hill et al. | |
| 6,537,228 B1 | 3/2003 | Lambert | |
| 6,542,774 B2 | 4/2003 | Hill et al. | |
| 6,587,726 B2 | 7/2003 | Lurie et al. | |
| 6,589,188 B1 | 7/2003 | Street et al. | |
| 6,641,542 B2 | 11/2003 | Cho et al. | |
| 6,684,101 B2 | 1/2004 | Daum | |
| 6,714,823 B1 | 3/2004 | De Lurgio et al. | |
| 6,718,208 B2 | 4/2004 | Hill et al. | |
| RE38,705 E | 2/2005 | Hill et al. | |
| 6,881,192 B1 | 4/2005 | Park | |
| 6,890,306 B2 | 5/2005 | Poezevera | |
| 6,928,324 B2 | 8/2005 | Park et al. | |
| 6,934,583 B2 | 8/2005 | Weinberg et al. | |
| 6,937,903 B2 | 8/2005 | Schuler et al. | |
| 6,964,641 B2 | 11/2005 | Cho et al. | |
| 7,025,730 B2 | 4/2006 | Cho et al. | |
| 7,070,568 B1 | 7/2006 | Koh | |
| 7,077,132 B2 | 7/2006 | Berthon-Jones | |
| 7,082,331 B1 | 7/2006 | Park et al. | |
| 7,094,207 B1 | 8/2006 | Koh | |
| 7,155,278 B2 | 12/2006 | King et al. | |
| 7,179,229 B1 | 2/2007 | Koh | |
| 7,184,829 B2 | 2/2007 | Hill et al. | |
| 7,200,442 B1 | 4/2007 | Koh et al. | |
| 7,212,862 B2 | 5/2007 | Park et al. | |
| 7,223,244 B1 | 5/2007 | Koh | |
| 7,225,019 B2 | 5/2007 | Jahns et al. | |
| 7,225,021 B1 | 5/2007 | Park et al. | |
| 7,245,971 B2 | 7/2007 | Park et al. | |
| 7,269,457 B2 | 9/2007 | Shafer et al. | |
| 7,269,459 B1 | 9/2007 | Koh | |
| 7,277,757 B2 | 10/2007 | Casavant et al. | |
| 7,340,302 B1 | 3/2008 | Falkenberg et al. | |
| 7,357,775 B1 | 4/2008 | Koh | |
| 7,361,146 B1 | 4/2008 | Bharmi et al. | |
| 7,363,086 B1 | 4/2008 | Koh et al. | |
| 7,371,220 B1 | 5/2008 | Koh et al. | |
| 7,628,801 B2 | 12/2009 | Westlund et al. | |
| 7,647,115 B2 | 1/2010 | Levin et al. | |
| 7,747,323 B2 | 6/2010 | Libbus et al. | |
| 7,787,946 B2 | 8/2010 | Stahmann et al. | |
| 8,086,314 B1 | 12/2011 | Kieval | |
| 8,131,372 B2 | 3/2012 | Levin et al. | |
| 8,200,336 B2 | 6/2012 | Tehrani et al. | |
| 8,244,359 B2 | 8/2012 | Gelfand et al. | |
| 8,255,056 B2 | 8/2012 | Tehrani | |
| 8,280,513 B2 | 10/2012 | Tehrani et al. | |
| 8,290,595 B2 | 10/2012 | Kieval et al. | |
| 8,348,941 B2 | 1/2013 | Tehrani | |
| 8,463,401 B2 | 6/2013 | Jones et al. | |
| 10,406,366 B2 | 9/2019 | Westlund et al. | |
| 10,518,090 B2 | 12/2019 | Gelfand et al. | |
| 2001/0003799 A1 | 6/2001 | Boveja | |
| 2002/0165535 A1 | 11/2002 | Lesh et al. | |
| 2002/0165536 A1 * | 11/2002 | Kelley | A61N 1/05 606/41 |
| 2003/0050681 A1 * | 3/2003 | Pianca | A61N 1/057 607/125 |
| 2003/0195571 A1 | 10/2003 | Burnes et al. | |
| 2004/0088015 A1 | 5/2004 | Casavant et al. | |
| 2005/0043765 A1 | 2/2005 | Williams et al. | |
| 2005/0061320 A1 | 3/2005 | Lee et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0165457 A1 | 7/2005 | Benser et al. | |
| 2005/0197588 A1 | 9/2005 | Freeberg | |
| 2005/0240240 A1 | 10/2005 | Park et al. | |
| 2005/0288729 A1 | 12/2005 | Libbus et al. | |
| 2005/0288759 A1 | 12/2005 | Jones et al. | |
| 2006/0030894 A1 | 2/2006 | Tehrani | |
| 2006/0036294 A1 | 2/2006 | Tehrani | |
| 2006/0041277 A1 * | 2/2006 | Deem | A61N 1/36128 607/3 |
| 2006/0041295 A1 * | 2/2006 | Osypka | A61N 1/0558 607/117 |
| 2006/0084060 A1 | 4/2006 | Nagahama et al. | |
| 2006/0122662 A1 | 6/2006 | Tehrani et al. | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0229677 A1 * | 10/2006 | Moffitt | A61N 1/37217 607/2 |
| 2006/0247729 A1 | 11/2006 | Tehrani et al. | |
| 2006/0247750 A1 | 11/2006 | Seifert et al. | |
| 2007/0021795 A1 | 1/2007 | Tehrani | |
| 2007/0118183 A1 | 5/2007 | Gelfand et al. | |
| 2007/0129643 A1 | 6/2007 | Kwok et al. | |
| 2007/0260285 A1 | 11/2007 | Libbus et al. | |
| 2007/0282376 A1 * | 12/2007 | Shuros | A61N 1/36114 607/2 |
| 2008/0154330 A1 | 6/2008 | Tehrani et al. | |
| 2008/0161878 A1 | 7/2008 | Tehrani et al. | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0183264 A1 | 7/2008 | Bly et al. | |
| 2008/0188903 A1 | 8/2008 | Tehrani et al. | |
| 2008/0188904 A1 | 8/2008 | Tehrani et al. | |
| 2009/0036947 A1 | 2/2009 | Westlund et al. | |
| 2013/0165989 A1 | 6/2013 | Gelfand et al. | |
| 2016/0001072 A1 | 1/2016 | Gelfand et al. | |
| 2022/0176119 A1 | 6/2022 | Gelfand et al. | |

OTHER PUBLICATIONS

Shaul, Donald B., et al., Thoracoscopic Placement of Phrenic Nerve Electrodes for Diaphragmatic Pacing in Children, Journal of Pediatric Surgery, vol. 37, No. 7, pp. 974-978, 2002.

Office Action from corresponding Canadian Patent Application No. 2,865,410, dated Feb. 3, 2021.

Redline, Susan et al., Beyond the Fat Boy, Journal of Applied Physiology 2005, vol. 99: pp. 1243-1244.

Esler, Murray et al., Is Obstructive Sleep Apnea the Cause of Sympathetic Nervous Activation in Human Obesity?, Journal of Applied Physiology 2006, vol. 100, pp. 11-12.

Caples, Sean M. et al., Influence of Cardiac Function and Failure on Sleep-Disordered Breathing, Journal of Applied Physiology 2005, vol. 99, pp. 2433-2439.

Punjabi, Naresh M. et al., Disorders of Glucose Metabolism in Sleep Apnea, Journal of Applied Physiology 2005, vol. 99, pp. 1998-2007.

Leuenberger, Ursa. et al., Hypoxia Augments Apnea-Induced Peripheral Vasoconstriction in Humans, Journal of Applied Physiology 2001, vol. 90, pp. 1516-1522.

(56) References Cited

OTHER PUBLICATIONS

Oliven, Arie, et al., Upper Airway Response to Electrical Stimulation of the Genioglossus in Obstructive Sleep Apnea, Journal of Applied Physiology 2003, vol. 95, pp. 2023-2029.
Parati, Gianfranco et al., Sleep Apnea: Epidemiology, Pathophysiology, and Relation to Cardiovascular Risk, Am Journal Physiological Society 2007, vol. 293, pp. R1671-R1683.
Gottfried, Stewart B. et al., Effects of Phrenic Stimulation on Upper Airway Resistance in Anesthetized Dogs, Am Physiological Society 1983, 0161-7567/83, pp. 419-426.
Planas, Roque F. et al., Diaphragmatic Pressures: Transvenous vs. Direct Phrenic Nerve Stimulation, Am Physiological Society 1985, 0161-7567/85, pp. 269-273.
Series, F. et al., Site of Phrenic Nerve Stimulation-Induced Upper Airway Collapse: Influence of Expiratory Time, Journal of Applied Physiology 2002, vol. 92, pp. 665-671.
Kingma, John G. Jr. et al., Neuromodulation Therapy Does Not Influence Blood Flow Distribution or Left-Ventricular Dynamics During Acute Myocardial Ischemia, Autonomic Neuroscience: Basic and Clinical 91 (2001) pp. 47-54.
Linderoth, Bengt, MD, PHD et al., Mechanisms of Spinal Cord Stimulation in Painful Syndromes: Role of Animal Models, American Academy of Pain Medicine, vol. 7, No. S14-S26, 2006.
Tanaka, Satoshi et al., Mechanisms of Sustained Cutaneous Vasodilation Induced by Spinal Cord Stimulation, Autonomic Neuroscience: Basic and Clinical114 (2004) pp. 55-60.
Lorenzi-Filho, Geraldo et al., Cheyne-Stokes Respiration in Patients with Congestive Heart Failure: Causes and Consequences, Clinics 2005; 60(4):333-44.
Brack, Thomas, Cheyne-Stokes Respiration in Patients with Congestive Heart Failure, Swiss Med Wkly 2003; 133:605-610, www.smw.ch.
Yumino, Dai et al., Central Sleep Apnea and Cheyne-Stokes Respiration, Proceedings of the American Thoracic Society, 2008, vol. 5, pp. 226-236.
Garrido-Garcia, H. et al., Treatment of Chronic Ventilatory Failure Using a Diaphragmatic Pacemaker, Spinal Cord (1998) 36, 310-314.
Diedrichs, Holger et al., Symptomatic Relief Precedes Improvement of Myocardial Blood Flow in Patients Under Spinal Goard Stimulation, BioMed Central, 2005, pp. 1-7.
Kaneko, S. et al., A New Approach to Respiratory Assist for Phrenic Nerve Paralysis, Trans Am Soc. Artif Intern Organs, 1985, vol. XXXI, pp. 301-304.
MacIntyre, Neil R., MD, Setting the Frequency-Tidal Volume Pattern, www.rcjournal.com/contents/03.02/03.02.0266.asp.
Kohnlein, T. et al., Central Sleep Apnoea Syndrome in Patients with Chronic Heart Disease: A Critical Review of the Current Literature, Thorax 2002; 57:547-554.
Javaheri, Shahrokh, MD, Central Sleep Apnea in Congestive Heart Failure: Prevalence, Mechanisms, Impact, and Therapeutic Options, Seminars in Respiratory and Critcal Care Medicine, 2005, vol. 26, No. 1.
Dobelle, William H., Use of Breathing Pacemakers to Suppress Intractable Hiccups of up to Thirteen Years Duration, ASAIO Journal1999, pp. 524-525.
Series, Frederic, Assessment of Upper Airway Dynamics in Awake Patients with Sleep Apnea Using Phrenic Nerve Stimulation, Am Journal Respir Crit Care Med, 2000, vol. 162., pp. 795-800.
Bilgutay, A.M. et al., Augmented Ventilation by Synchronous Phrenic Nerve Stimulation, Trans. Amer. Soc. Artif. Int. Organs, 1970, vol. XVI, pp. 213-217.
Yasuma, Fumihiko et al., Eight-Year Follow-Up Study of a Patient with Central Alveolar Hypoventilation Treated with Diaphragm Pacing, Respiration, 1998; 65:313-316.
Handa, Y. et al., Basic Studies on Electrophrenic Respiration Part 2—Assisted Ventilation by the Synchronous Electrophrenic Respirator, Medical and Biological Engineering, Jul. 1976.
Kimura, M. et al., A Heart-Rate-Responsive Diaphragm Pacemaker, Med. & Biol. Eng. & Comput., 1987, 25, 458-462.
Kimura, M. et al., Heart Rate and Body Temperature Sensitive Diaphragm Pacing, Med. & Bioi. Eng. & Comput. 1992,30, 155-161.
Kimura, M. et al., Addition to an RF-Coupled Phrenic Nerve Stimulator Implant to Provide Outward Transmission of Body Temperature, Med. & Bioi. Eng. & Comput. 1986, 24, 659-661.
Taira, Takaomi, MD, Ph.D et al., Phrenic Nerve Stimulation for Diaphragm Pacing with a Spinal Cord Stimulator, Elsevier Science, Surg Neural, 2003; 59:128-32.
Chatfield, Paul 0. et al., Role of Pulmonary Proprioceptive Reflexes in Suppression of Spontaneous Breathing During Electrophrenic Respiration, Dept. of Physiology, Harvard Medical School, and Dept. of Physiology, Harvard School of Public Health, vol. 163.
Sarnoff, Stanley J. et al., Electrophrenic Respiration. III. Mechanism of the Inhibition of Spontaneous Respiration, Dept. of Physiology, Harvard School of Public Health, 1948, vol. 155, pp. 203-207.
Sarnoff, Stanley J. et al., Electrophrenic Respiration IV. The Effectiveness of Contralateral Ventilation During Activity of One Phrenic Nerve, Dept. of Physiology, Harvard School of Public Health, 1949, pp. 929-937.
Stemmer, Edward A. MD et al., Diaphragmatic Pacing in the Treatment of Hypoventilation Syndrome, Journal of Thoracic and Cardiovascular Surgery, vol. 54, No. 5, 1967, pp. 649-657.
Furman, Seymour, MD et al., Transvenous Stimulation of the Phrenic Nerves, Journal of Thoracic and Cardiovascular Surgery, vol. 62, No. 5, 1971, pp. 743-751.
Aiyar, Harish et al., Diaphragm Pacing for Chronic Respiratory Insufficient, CRC Press, LLC, 2001, Chapter 9.
International Search Report of international application PCT/US2006/044788 (Aug. 15, 2007). 3 pp.
Written Opinion of the International Searching Authority of international application PCT/US2006/044788 (Apr. 12, 2007). 3 pp.
International Preliminary Report on Patentability of international application PCT/US2006/044788 (May 20, 2008). 4 pp.
Prosecution History for corresponding U.S. Appl. No. 13/538,713 including: Notice of Allowance and Fee(s) Due mailed Aug. 19, 2019, Final Rejection mailed May 15, 2019, Non-Final Rejection mailed Nov. 2, 2018, Final Rejection mailed Aug. 9, 2017, Non-Final Rejection mailed Nov. 9, 2016, Final Rejection mailed Jan. 15, 2016, Non-Final Rejection mailed Apr. 14, 2015, Final Rejection mailed Apr. 21, 2014; and Non-Final Rejection mailed Jun. 19, 2013.
Prosecution History for corresponding U.S. Appl. No. 11/601,150 including: Notice of Allowance and Fee(s) Due mailed Jun. 4, 2012, Final Rejection mailed Jun. 8, 2010, Non-Final Rejection mailed Aug. 20, 2009; and Requirement for Restriction/Election mailed Mar. 23, 2009.
Prosecution History for corresponding U.S. Appl. No. 14/715,128 including: Advisory Action mailed Feb. 19, 2021, Final Rejection mailed Dec. 9, 2020, Non-Final Rejection mailed Jun. 5, 2020, Advisory Action mailed Mar. 3, 2020, Final Rejection mailed Nov. 14, 2019, Non-Final Rejection mailed Jun. 26, 2019, Advisory Action mailed May 21, 2019, Final Rejection mailed Jan. 23, 2019, Non-Final Rejection mailed Mar. 12, 2018; and Requirement for Restriction/Election mailed May 2, 2017.
Prosecution History for corresponding U.S. Appl. No. 12/150,654 including: Notice of Allowance and Fee(s) Due mailed Apr. 30, 2019, Non-Final Rejection mailed Apr. 6, 2018, Final Rejection mailed Mar. 2, 2017, Non-Final Rejection mailed May 5, 2016, Final Rejection mailed Jul. 30, 2013, Non-Final Rejection mailed Oct. 11, 2012, Non-Final Rejection mailed Dec. 19, 2011; and Requirement for Restriction/Election mailed May 16, 2011.

* cited by examiner

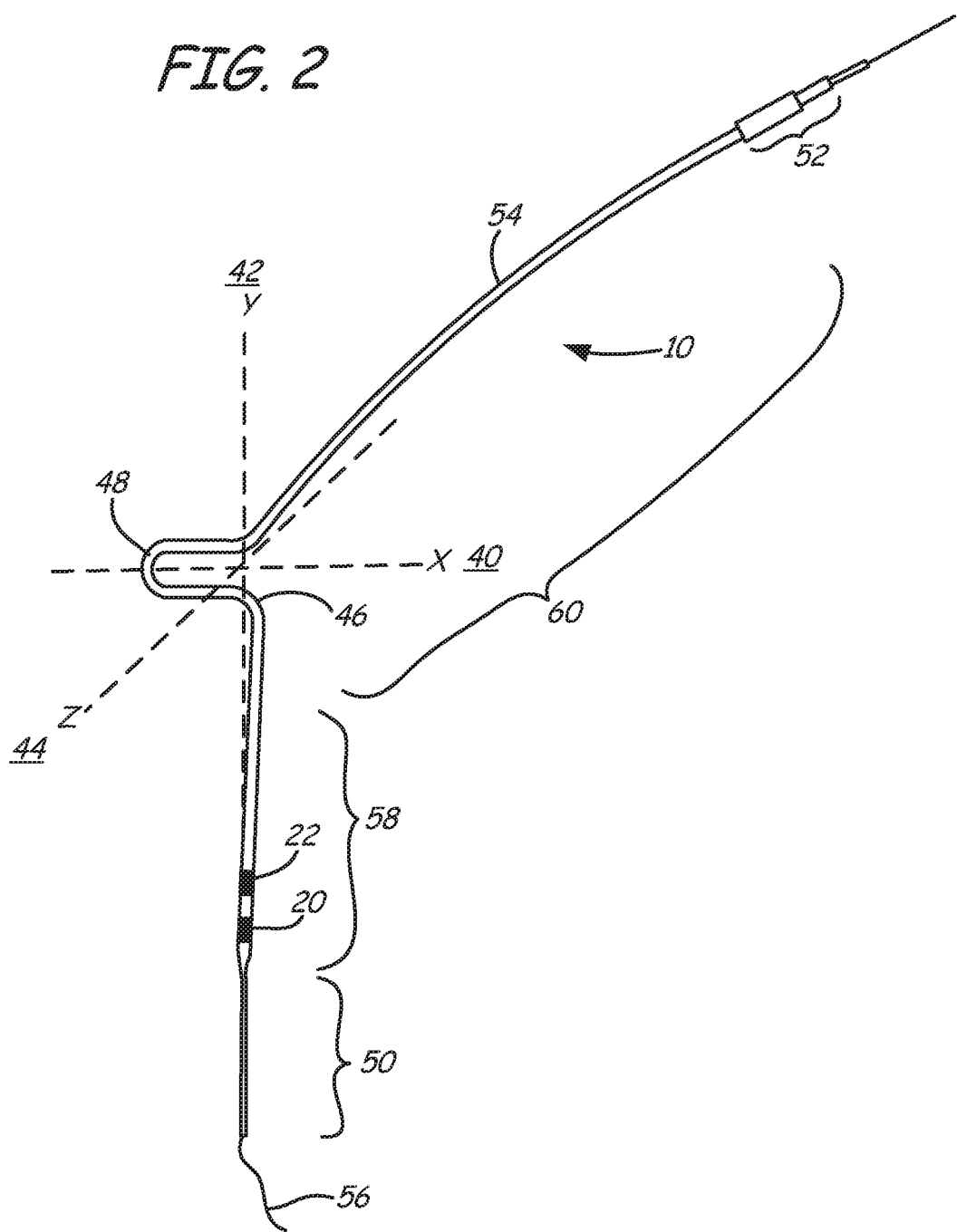

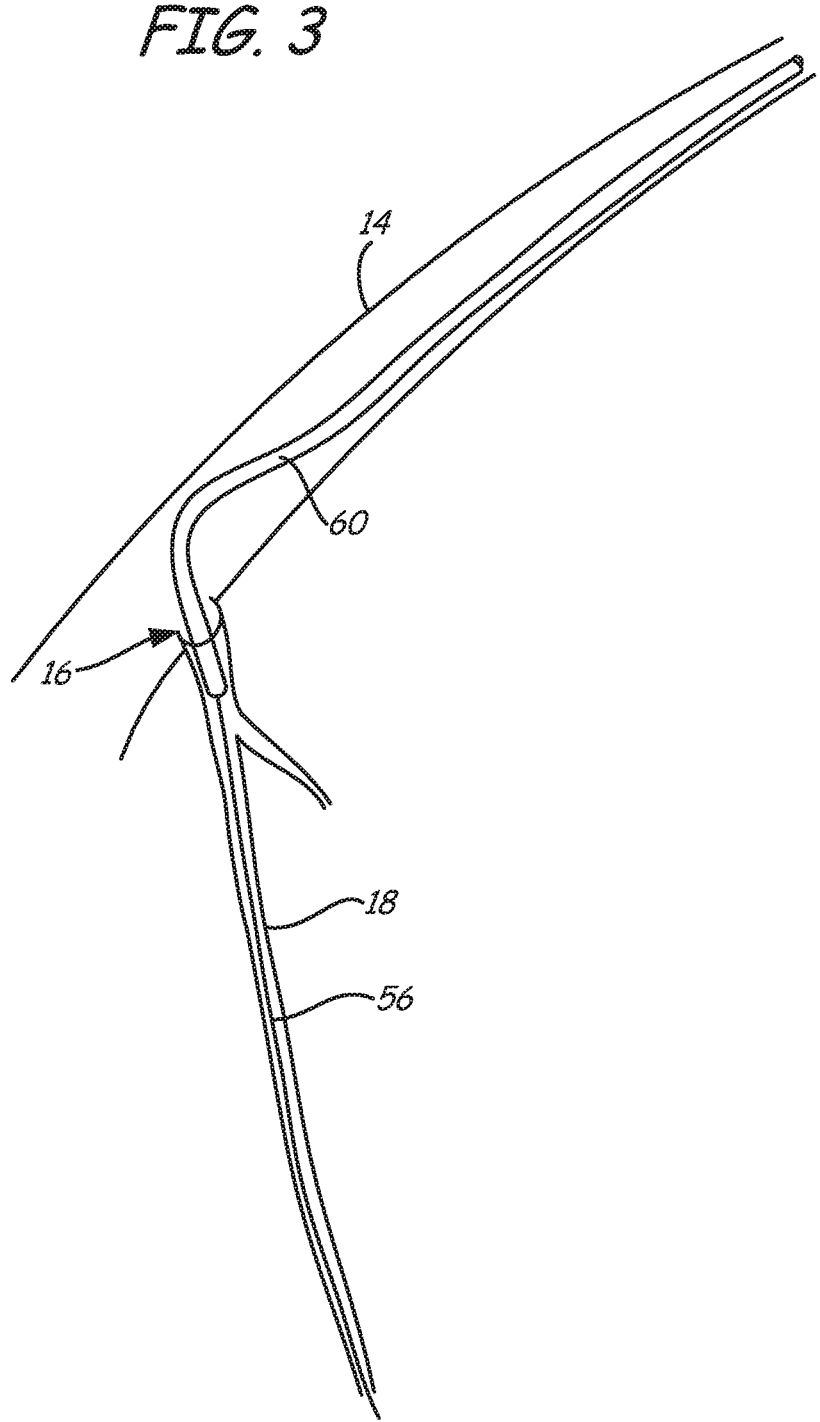

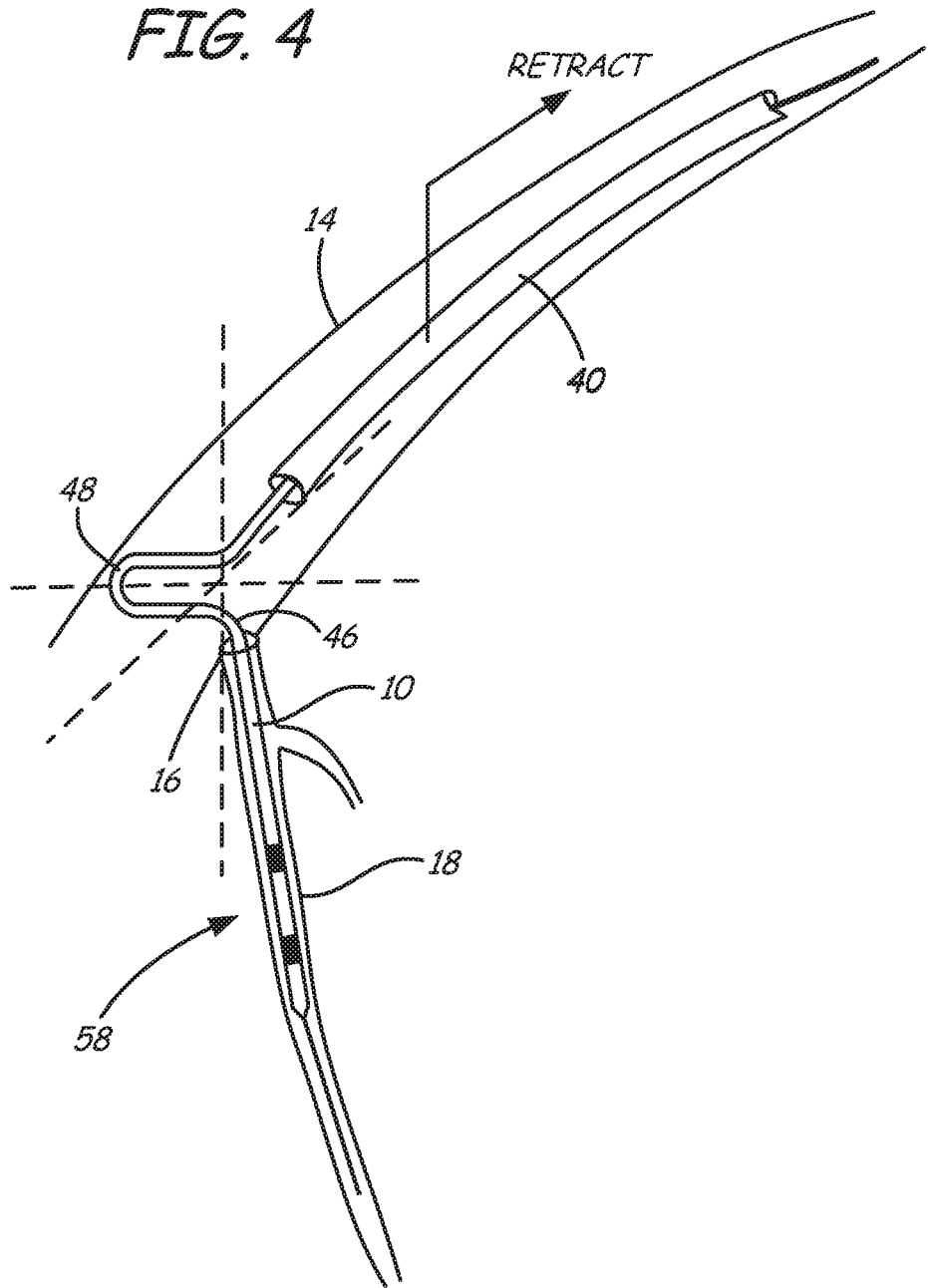

TRANSVENOUS PHRENIC NERVE STIMULATION SYSTEM

CROSS REFERENCE TO RELATED CASES

This application is a continuation of U.S. patent application Ser. No. 12/150,654 filed Apr. 30, 2008 titled "Transvenous Phrenic Nerve Stimulation System," now U.S. Pat. No. 10,406,366, which claims the benefit of and incorporates by reference U.S. Provisional Application 60/926,910 filed Apr. 30, 2007 titled "Leads for Transvenous Phrenic Stimulation." U.S. patent application Ser. No. 12/150,654 also claims the benefit of and incorporates by reference and is a continuation-in-part of U.S. Utility application Ser. No. 11/601,150 filed Nov. 17, 2006 titled "System and Method to Modulate Phrenic Nerve to Prevent Sleep Apnea," now U.S. Pat. No. 8,244,359, which claims the benefit of U.S. Provisional Application 60/737,808 filed Nov. 18, 2005 titled "System and Method to Modulate Phrenic Nerve to Prevent Sleep Apnea," U.S. Provisional Application 60/743,062 filed Dec. 21, 2005 titled "System and Method to Modulate Phrenic Nerve to Prevent Sleep Apnea," and U.S. Provisional Application 60/743,326 filed Feb. 21, 2006 titled "System and Method to Modulate Phrenic Nerve to Prevent Sleep Apnea."

FIELD OF THE INVENTION

The present invention relates generally to a method of implanting a phrenic nerve stimulation lead system and a related phrenic nerve stimulation lead for use with an implanted pulse generator (IPG) for treating a breathing disorder.

BACKGROUND OF THE INVENTION

Many patients with breathing disorders such as central sleep apnea (CSA) display periods of rapid respiration followed by a relatively long compensatory pause in respiration. The clinical manifestation of the disorder is a period of shallow rapid breathing followed by frank apnea or hypopnea. This pattern repeats episodically and is called Cheyne Stokes Respiration (CSR). Several treatment regimes have been proposed to alleviate CSR, including a technique presented in detail in the utility application incorporated by reference.

Historically, the ability to control respiration via phrenic nerve stimulation is widely known and well reported in the literature. Early work shows the use of phrenic nerve stimulation to treat paralyzed patients to initiate and support respiration. A substantial body of animal research discloses the basic mechanisms for respiration control though stimulation of the phrenic nerve.

Although phrenic nerve stimulation is known in the art there is a continuing need to improve the "leads" devices for accessing and electrically stimulating the phrenic nerve. And there is a continuing need to improve the stimulation methodology.

SUMMARY OF THE INVENTION

The phrenic nerve stimulation lead device has a flexible elongate lead body with a proximal connector and a distal tip. In use the lead is permanently implanted in a vein near one portion of the phrenic nerve. The lead has physical features and properties important for successful transvenous deployment and stimulation of the phrenic nerve from the left pericardiophrenic vein.

The stimulation lead has a distal tip tapered into a "rats tail". The presence of this extended tapered section will serve to orient and stabilize the lead and the electrodes in the vessel by restricting movement of the lead with respect to the vessel. The additional surface area of the lead provides additional friction and ensures that the vessel and lead do not move relative to each other. One or more and preferably two electrode sites are placed proximal of this distal tip. Each electrode is typically formed as a ring and individually electrically coupled to the proximal connector by internal conductors within the lead.

In one embodiment a guidewire lumen is carried entirely through the lead body and the lumen is concentric with the distal tip at the distal tip. In an alternate embodiment the lead is stiffened by a removable stylet that is inserted into the lead into a stylet lumen.

An optional mechanical stop feature may be included within the lead body to intercept and interact with a finishing guide wire to stabilize the lead during placement.

The lead is acutely repositionable but anticipated foreign-body response will render it permanent in the vessel. The lead may have steroid eluting features to regulate this physiologic process.

The shape of the lead body includes two or more curves, bends or loops near the distal end of the lead. These curves in the lead body lie in two planes and direct the tip at an angle. These features stabilize the lead in a large companion vessel while biasing the distal "rats tail" into a stable position in the smaller target vessel.

The preferred implantation process requires a percutaneous puncture to access the subclavian vein. The implanted pulse generator (IPG) will be implanted in a subcutaneous pocket nearby. A guide catheter having a shaped tip is navigated along the subclavian vein using a guidewire. The catheter and wire pass through the brachiocephalic vein in to the ostium of the left pericardiophrenic vein. Normal contrast venography techniques are used to illuminate and access this location. The guidewire is inserted several centimeters into the left pericardiophrenic vein and the mouth of the guide catheter is passed into the ostium of the left pericardiophrenic vein. Next the stimulation lead is delivered to a target location through the guide catheter over the guidewire alone or with the use of a stylet. When the electrodes are well positioned near the phrenic nerve target location the stylet or guidewire is removed and the optional stabilizing or finishing guidewire wire is exchanged and inserted into the lead body. Relative traction between the finishing guide wire and the guide sheath allows for the smooth removal of the guide catheter without dislodging the lead. In essence the "rats tail" remains biased and stationary in the left pericardiophrenic vein as the lead "relaxes" and assumes its natural low mechanical energy state while the guide catheter is removed. Withdrawal of the finishing wire if used or the guidewire or stylet activates the complementary shaped curves of the lead. As the curves bend and unfurl into contact with the larger brachiocephalic vein the most distal tip of the of the lead in the smaller vessel becomes stabilized. Next the proximal connector of the lead is coupled to the IPG. The IPG provides stimulation that completes the implantation method and the method of therapy.

BRIEF DESCRIPTION OF THE DRAWINGS

Identical reference numerals indicate identical features throughout the figures of the drawing, wherein:

FIG. 2 depicts the lead device;

FIG. 3 depicts a step in method used to implant the device;

FIG. 4 depicts the lead in position in the target vessel with the electrodes positioned at the target location.

DETAILED DESCRIPTION OF THE INVENTION

Stimulation Regime

Figure 1:
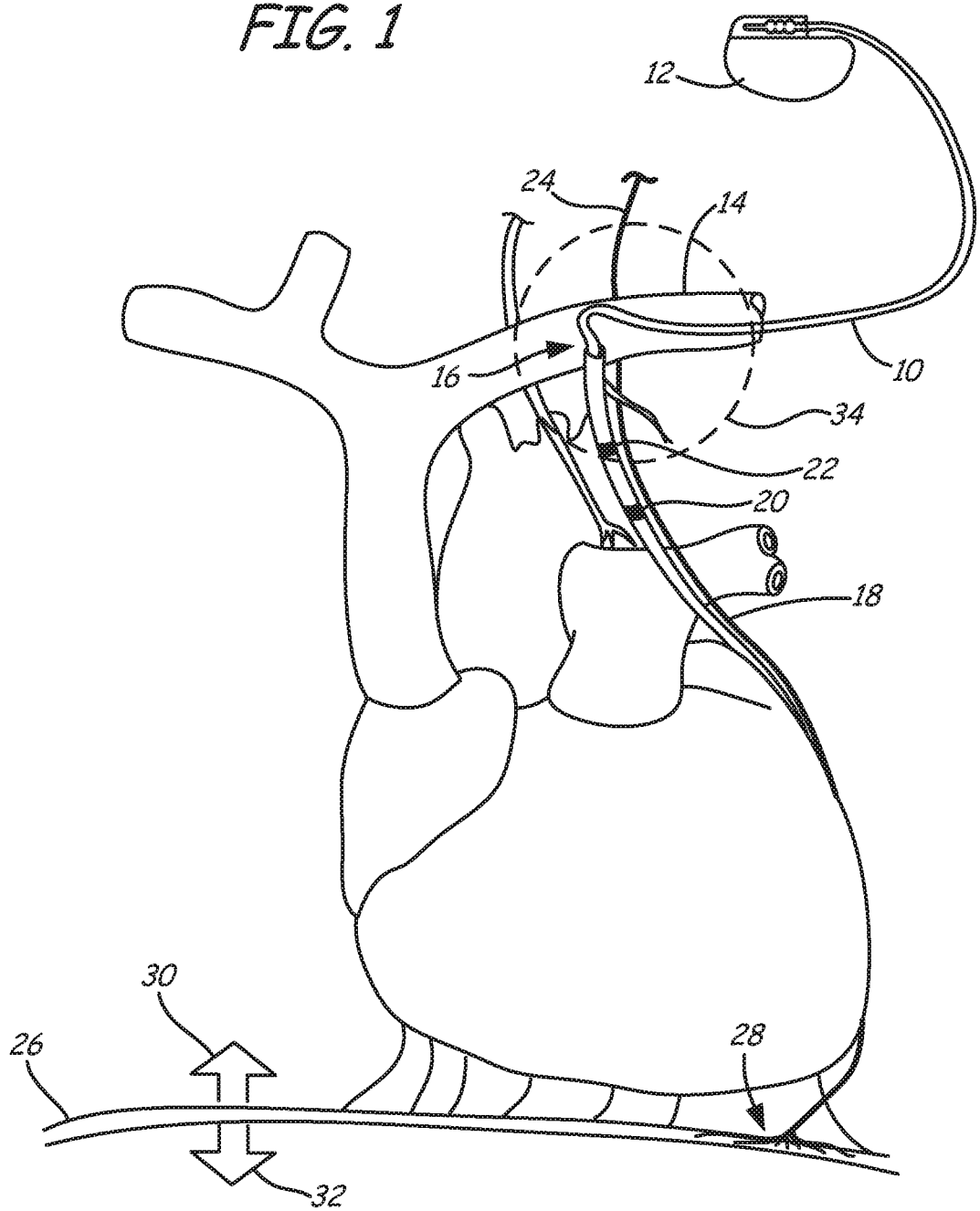
FIG. 1 depicts the implanted system.

The applicant has incorporated a utility patent reference that discloses in detail a medical device (IPG) that can detect and treat CSR and other forms of breathing disorders by the transvenous electrical stimulation of the phrenic nerve.

For purposes of this disclosure it is sufficient to understand that the disclosed technique uses electrical stimulation of one phrenic nerve to arrest or still the motion of one hemidiaphragm of the patient. This process lowers the observed breathing rate post therapy and over time drives the blood gases to an improved state of oxygen saturation and carbon dioxide elimination.

The implanted pulse generator (IPG) 12 has the ability to detect the respiration process in real time. Preferably impedance plesthysmography is used to detect both the rate of respiration and the turning points within a single breath. It is anticipated that the companion IPG 12 includes an impedance plethysmograph that emits minute electrical pulses between electrodes on a measurement lead system (not shown in the present figures). These impedance signals are used to measure the volume of the lung and rate of change of volume of the lung.

The phrenic nerve stimulation therapy is provided after the start of a breath but before the natural end of the breath. The magnitude of the stimulation is sufficient to arrest the motion of the diaphragm. By essentially stopping the breathing for a moment the overall duration of the breath is extended. This breath hold process lowers the observed rate of breathing of at least one lung.

This stimulation therapy may be supplied to each breath for a series of breaths or on a less frequent basis. The stimulation may be supplied in response to a detected episode of CSR or it may be provided to prevent progression to CSR. For example, stimulation may be initiated upon the detected occurrence of CSR. Alternatively an activity sensor may report that the patient is supine and at rest and this set of criteria may be necessary and sufficient to invoke therapeutic stimulation. Regardless of the specific intervention criteria, the IPG will delivery the appropriate amount of energy to still the breath, via the transvenous stimulation lead.

System Architecture

FIG. 1 depicts the overall architecture and context of the therapy where the lead 10 coupled to an implanted pulse generator 12. The lead is inserted through the brachiocephalic vein 14 into the ostium 16 of the left pericardiophrenic vein 18. In this chronic condition the two electrodes 20 and 22 can deliver electrical stimulation to the phrenic nerve 24, which courses parallel to the vein 18 in this target vessel at this target location. This half of the branching phrenic nerve 24 terminates in the hemidiaphragm 26 as indicated by the innervations depicted at location 28. The nerve innervations excite the muscles of the hemidiaphragm which move downward as indicated by motion arrows 32 to produce inspiration followed by upward motion as indicated by motion arrow 30 to produce expiration. Together the motion arrows represent rhythmic respiration. For purposes of orientation other familiar anatomic structures are seen but not labeled in the figure.

In summary after implantation the lead 10 system delivers electrical stimulation to the phrenic nerve to arrest diaphragm 26 motion by the delivery of electrical energy after the onset of inspiration indicated by motion arrow 32 in the figure and the electrical energy delivered is sufficient to pause that diaphragm motion. In this fashion the lead 10 system and the IPG 12 are used for stimulating the phrenic nerve 24 of a patient to treat defects in respiration.

Stimulation Lead

FIG. 2 depicts the lead system 10 in isolation. The lead is best considered by dividing it up into various segments. The most distal segment 50 takes the form of a narrow taper. This "rats tail" is coupled to a stimulation segment 58 that includes a first electrode 22 and a second electrode 20. Although the preferred exemplary embodiment shows two electrodes, other numbers of electrodes are operable and desirable in some situations. The electrode placement on the leads seen in the figures is desirable because to the extent possible it is desired to have the stimulation current path transect the longitudinal fibers of the phrenic nerve 24 at the target location. It has been determined experimentally that this orientation reduces thresholds for stimulation of the nerve.

Next, an intermediate shaped segment is shown at numeral 60. The shaped segment includes two or more bends or loops or curves. The bend curve 48 lies in the XZ plane in the figure. The bend curve 46 rises out of the XZ plane in the Y direction. Preferably the axis of the distal segment 50 makes an included angle of about 15 degrees with respect to the XZ plane.

The most proximal segment includes a connector pin assembly 52 that allows conductors within the lead to communicate with the two electrodes. For clarity the conductors are not shown. The construction of the conductors is well known in this art and need not be shown in detail. Preferably and overall the elongate portion 54 of the shaped segment 60 and the distal segment 50 are not coplanar and the major axis of the elongate portion 54 and major axis of the distal segment 50 are not coaxial. These geometric constraints place the elongate segment 54 and the distal segment 50 in separate planes and the major axes of these sections of the lead are not collinear.

FIG. 2 shows the lead 10 in isolation in its low stress state. The lead has a natural neutral bias in the figure and the lead structure and shape gives rise to a friction zone caused by a in-plane deflection of the lead around first primary radius of bend curve 48 and a secondary radius of bend curve 46. In use the curvilinear structures will permit the stable positioning of the lead body in the brachiocephalic vein and permit entry of the stimulation segment into the ostium of the left pericardiophrenic vein and stabilize the electrodes at the target location.

The lead may also have a through lumen to accept a guide wire 56 as depicted in the figure passing into the connector 52 pin and traveling beyond the distal tip and emerging at reference numeral 56. As an alternative, a stylet lumen may be located within the lead to permit the use of a stylet to stiffen the lead. It may also be desirable to have a mechanical stop in the stylet or guide wire lumen to accept a "finishing wire". This optional finishing wire can be used to supply a force to the lead to keep it in position as the guide catheter is removed. In general the finishing wire is of slightly larger diameter and it bottoms out at a location near but still proximal of the electrode and shaped segments of the lead. Pulling on the guide catheter while pushing on the finishing wire at the same time prevents the lead to guide catheter friction from dislodging or moving the electrodes from their preferred location.

Method of Implantation

FIG. 3 is an enlarged portion of part of FIG. 1 designated by numeral 34 on FIG. 1. The brachiocephalic vein 14 and the branching left pericardiophrenic vein 18 are shown in isolation. The figure illustrates a method of implanting a lead in a small vein 18 that branches off from a large vein 14. The process begins with a "percutaneous stick" to access a large vein connecting to the brachiocephalic vein. A sharp hollow needle trocar enters the vein and a guidewire is advanced through the trocar into the vessel. The trocar is withdrawn over the wire and replaced with a sheath which is passed into the vessel. Next a guide wire and guide catheter of the type having a distal curve are navigated to the ostium 16 of the left pericardiophrenic vein. The curved tip for the guiding catheter is introduced in to this small vein. Venographic imaging technologies such as contrast injection and biplane fluoroscopy are used to locate the ostium 16. With both the guide wire and guide catheter in the small vein the lead 10 may be passed over the wire into the vein. Under contrast imaging and temporary stimulation the best spot for activating the phrenic nerve is located. This defines the target location. Next the guidewire and guiding catheter are carefully removed while holding the lead in position with the optional finishing wire if present. The finishing wire if used compensates for the friction between the guide catheter 60 and the lead 10 which would otherwise causes the guide catheter to tend to drag the lead out of position as the guide catheter is removed.

Lead Interactions

Turning to FIG. 4 once again there is a shown an enlarged section of FIG. 1 indentified in that figure by reference numeral 34. FIG. 4 shows the lead 10 delivered through a guide sheath 40. A stylet or guidewire (GW) may be inserted into the lead 10 to straighten and stiffen the structure. Once the lead enters the target vessel the stylet may be removed and the lead adopts its low stress state in the vessel. In this figure the biasing mechanism 46 is shown in contact with the walls of the vessel 18. The bend 48 lies in a single plane in contact with the wall of vessel 14. The bend or shape 46 exerts a force against the ostium 16 to help anchor the electrodes and stimulation segment in the smaller target vessel 18.

Steroid eluting features may be provided on portions of the lead system to reduce inflammation associated with the placement of the leads. Other coatings maybe used to enhance or reduce friction to help stabilize the lead.

What is claimed is:

1. An electrical stimulation lead for delivering energy to a nerve lying close to a vein of a patient comprising:
   an elongate lead body having a proximal end and a distal end;
   a plurality of electrodes to stimulate a phrenic nerve of the patient, the plurality of electrodes being located along the elongate lead body near the distal end;
   a proximal connector included in the proximal end and having an electrical connection;
   a plurality of conductors located in an interior of the elongate lead body connecting each electrode of the plurality of electrodes to the electrical connection; and
   a plurality of bend curves, all of the plurality of bend curves being free of any of the plurality of electrodes and having arcuate shapes to cause a bias force to be exerted by the electrical stimulation lead to maintain the distal end substantially immobile in a pericardiophrenic vein of the patient, wherein at least one bend curve of the plurality of bend curves is configured to apply a bias force to a vessel wall of the pericardiophrenic vein, wherein the at least one bend curve is shaped to deflect around a radius such that the bias force stabilizes the plurality of electrodes in the pericardiophrenic vein.

2. The electrical stimulation lead of claim 1, wherein a first section of the elongate lead body lies in a first plane and a second section of the elongate lead body lies in a second plane which intersects the first plane.

3. The electrical stimulation lead of claim 2, wherein the second plane intersects the first plane at an angle of about 15 degrees.

4. The electrical stimulation lead of claim 2, wherein the second section of the elongate lead body terminates in a tapered distal tip segment.

5. The electrical stimulation lead of claim 1, wherein the distal end of the elongate lead body terminates in a tapered distal tip segment.

6. The electrical stimulation lead of claim 5, wherein at least one of the plurality of electrodes is disposed proximal of the tapered distal tip segment.

7. The electrical stimulation lead of claim 1, wherein the plurality of electrodes includes only two electrodes.

8. The electrical stimulation lead of claim 1, wherein the elongate lead body includes a stylet lumen extending partially through the elongate lead body.

9. The electrical stimulation lead of claim 1, wherein the elongate lead body includes a drug-eluting coating.

10. The electrical stimulation lead of claim 1, wherein the elongate lead body includes a guide wire lumen.

11. The electrical stimulation lead of claim 10, wherein the guide wire lumen extends entirely through the elongate lead body.

12. The electrical stimulation lead of claim 1, wherein the elongate lead body is configured to accept insertion of a guide wire for implantation of the elongate lead body in the pericardiophrenic vein of the patient.

13. The electrical stimulation lead of claim 12, wherein the guide wire is configured to straighten the elongate lead body.

* * * * *